Jan. 29, 1974 D. L. ARMSTRONG Plant Pat. 3,457
ROSE PLANT
Filed April 19, 1972
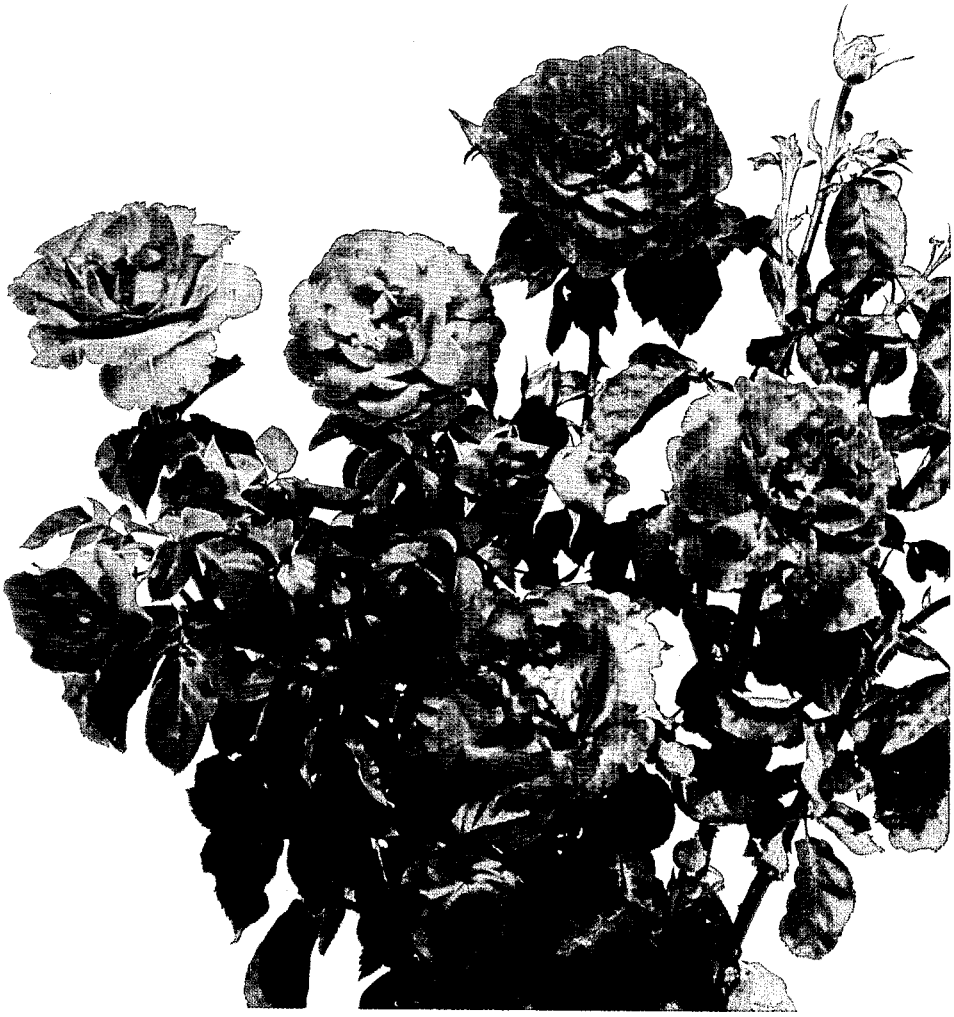

United States Patent Office

Plant Pat. 3,457
Patented Jan. 29, 1974

3,457

ROSE PLANT

David L. Armstrong, Upland, Calif., assignor to Armstrong Nurseries, Inc., Ontario, Calif.

Filed Apr. 19, 1972, Ser. No. 245,669
Int. Cl. A01h 5/00
U.S. Cl. Plt.—28 1 Claim

ABSTRACT OF THE DISCLOSURE

An asexually reproduced bush rose of the floribunda class particularly characterized in the color stability of the bright reddish orange petals of the bloom, which undergo little or no change in coloration or shade from first opening to late maturity, although flowers blooming in cool gray weather may be somewhat darker in shade throughout their life.

The plant is moderately low growing and moderately spreading in habit, carrying most of its flowers in small irregular clusters with strong peduncles on short to medium stems.

Only occasionally do the sepals have foliaceous parts extending beyond the bud. The buds are small, but the bloom appears to grow in size until the flower is fully open, at slightly less than three or four inches. The petals tend to be ruffled and fluted in form. Flowers are semi-double to double, comprising 19–25 petals and 2–8 petaloids, with little fragrance. The plant blooms almost continuously throughout the growing season, but makes a moderately massive display only at the first Spring blooming. After the petals have dropped, the peduncle also falls off.

This invention relates to a new variety of floribunda rose, of the bush type, grown as an outdoor seedling for cut flowers and garden decoration. It was propagated and grown in Ontario, Calif.

The plant is a seedling having as its seed parent Spartan (Plant Pat. No. 1,357) and as its pollen parent Angelique (Plant Pat. No. 1,390). It holds its distinguishing characteristics through succeeding propagations by budding.

The accompanying drawing illustrates the plant in color and shows the flowering thereof from bud to full bloom.

This new variety may be distinguished from its *seed* parent, Spartan, in the following characteristics:

Whereas the flower of Spartan usually has about 30 petals, this new cultivar has from 19 to 25. The flower of Spartan are very fragrant, whereas the flowers of this new cultivar have little or no fragrance. When grown under comparable conditions, the flowers of Spartan are substantially larger than the flowers of this new cultivar. The flowers of this new cultivar are substantially brighter reddish-orange in color, and their color has more constancy than Spartan. The growth habit of the Spartan plant is relatively upright, and taller than the plants of this new cultivar, which are moderately spreading and relatively short.

This new variety is distinguished from its *pollen* parent, Angelique, in the following respects:

Whereas the flowers of Angelique are coral-pink to salmon-pink and slightly fragrant, the flowers of this new variety are a deeper color, namely, a bright reddish-orange, and they have relatively little or no fragrance. The flowers of Angelique are from 2½" to 3" in diameter, while the flowers of this new variety are somewhat larger, that is from 2¾" to 3¾" in diameter. The long lasting quality of the flowers of this new variety, and particularly the color constancy, are substantially greater than in the flowers of Angelique. Although the plants of this new cultivar are somewhat low and spreading in habit, the plants of Angelique are even more low growing than its offspring.

The flowers of this new variety are borne either singly or several to a stem in an irregular cluster, on normal short to medium stems. The plant blooms freely to abundantly outdoors, and nearly continuously during the growing season. There is no fragrance.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average length, average caliper, and strong but sometimes bending, and has numerous stipitate glands. Its color is near Strong Yellow Green, 5GY 6/8, overlaid with near Dark Red, 2.5R 3/7, where exposed to sunlight.

Before the calyx breaks, the bud is small in size, short to medium in length, pointed and broadly ovoid.

As the calyx breaks, the color is between Strong Red, 5R 4/12, and Dark Red, 5R 3/7.

A finely wooly tomentum lines the inner surface of the sepals and the margins of alternate sepals. The margins of other sepals have numerous stipitate glands and small foliaceous appendages, foliaceous parts on tips of sepals usually projecting less than one-third the bud length beyond the bud tip. There are stipitate glands on the outer surface.

As the first petal opens, it is small to average in size, of medium length, and urn-shaped. The outer surface of the petal is near Strong Reddish Orange, 7.5R 5/13, overlaid where exposed to light while in the bud with near Strong Red, 5R 4/12. The base of the petal is near Brilliant Yellow Green, 2.5GY 9/8. The inner surface of the petal is also near Strong Reddish Orange, 7.5R 5/13, with the same coloration at the base, while along the inside midrib of some of the outside petals is a pubescent vegetative streak which is near Brilliant Yellow Green, 2.5GY 9/8.

The bud opens up well, and is not retarded or prevented from opening by cold, hot, wet, or dry weather.

BLOOM

When fully open, the bloom is average in size, being from 2¾" to 3¾" in diameter. The petalage is semi-double to double, with from 19 to 25 petals, plus from 2 to 8 petaloids irregularly arranged.

The form of the bloom is cupped at first, later remaining cupped or becoming flat to open. At first, the petals remain somewhat tightly cupped, with tips rolled slightly outward; later, at maturity, they become loosely cupped, with tips still slightly rolled outward.

The petals are medium to thick in texture, moderately leathery, with inside satiny and the outside shiny to satiny. The outside petals are very broadly ovate and sometimes scalloped, and usually with one or more notches. The intermediate petals are cordate to broadly ovate and scalloped, sometimes having from none to several notches. The inside petals are broadly ovate, often irregularly scalloped, and with or without notches. Their colors may be modified by being blotched, shaded and/or washed with other colors.

The following description applied to a *newly opened* flower grown outdoors in the month of October in Ontario, Calif. The colors given are typical for *warm, sunny weather.*

The outer surface of the outside petal was near Vivid Red, 5R 5/13, with an area at the base near Brilliant Yellow Green, 2.5GY 9/8. The inner surface of the outside petal was near Strong Reddish Orange, 7.5R 5/13, with an area at the base of near Brilliant Yellow Green, 2.5GY 9/8, and a pubescent vegetative streak of the same color along the inside midrib of some of the outside petals.

The outer surface of the intermediate petal was between Deep Pink, 2.5R 6/11, and Strong Red, 2.5R 5/12, with an area at the base near Brilliant Yellow Green, 2.5GY 9/8. The inside surface of the intermediate petal was brighter than, but near, Strong Reddish Orange, 7.5R 5/13, with an area at the base between white and Brilliant Yellow Green, 2.5GY 9/8.

The outer surface of the inner petal is between Deep Pink, 2.5R 6/11, and Strong Reddish Orange, 7.5R 5/13, with an area at the base between white and Brilliant Yellow Green, 2.5GY 9/8. The inner surface of the inner petal is between Vivid Red, 5R 5/13, and Strong Reddish Orange, 7.5R 5/13, with an area at the base between white and Brilliant Yellow Green, 2.5GY 9/8.

The following description applies to a *newly opened* flower grown outdoors in the month of October in Ontario, Calif., but in this case the bloom was *affected by cool weather*:

The area at the base of all petals, outer, intermediate and inner, was between white and Brilliant Yellow Green, 2.5GY 9/8, on both the inner and outer surfaces of the petals. As to the remaining area of the petals:

The outer surface of the outside petal was between Strong Red, 2.5R 5/12, and Deep Pink, 2.5R 6/11. The inside surface of the outside petal was between Strong Reddish Orange, 7.5R 5/13, and Strong Red, 5R 4/12.

The intermediate and the inner petals were of the same coloration, the outside surface of each ranging from a color between Deep Pink, 10RP 6/12, and Strong Purplish Red, 10RP 5/12, to a color between Deep Pink, 2.5R 6/11, and Strong Red, 2.5R 5/12. The inside surface of both the intermediate and the inner petals ranged from near Strong Reddish Orange, 7.5R 5/13, to near Dark Red, 2.5R 3/7.

The description which follows was made from a rose that was *open for three days,* having been grown outdoors in the month of October in Ontario, Calif. The colors given are typical for *warm, sunny weather.*

The outer surface of the outside petal was between Strong Red, 2.5R 5/12, and Deep Pink, 2.5R 6/11, with an area at the base between white and Brilliant Yellow Green, 2.5GY 9/8. The inside of the outside petal was between Deep Pink, 2.5R 6/11, and Vivid Red, 5R 5/13, with an area at the base also between white and Brillinat Yellow Green, 2.5GY 9/8.

The outer surface of the inside petal was the same as the outer surface of the outside petal, while the inside surface was near Strong Reddish Orange, 7.5R 5/13, with the area at the base also between white and Brilliant Yellow Green, 2.5GY 9/8.

The description which follows is of a rose which was *open for three days* outdoors in the month of October in Ontario, Calif., but was *affected by cool, overcast weather*:

The outside surface of the outer petal was between Strong Red, 2.5R 5/12, and Deep Pink, 2.5R 6/11, with an area at the base between white and Brilliant Yellow Green, 2.5GY 9/8. The inside surface of the outer petal was between Deep Pink, 2.5R 6/11, and Vivid Red, 5R 5/13, to near Strong Reddish Orange, 7.5R 5/13, sometimes overlaid near the margins with near Dark Red, 2.5R 3/7, with an area at the base between white and Brilliant Yellow Green, 2.5GY 9/8.

The outer surface of the inside petal was between Deep Pink, 2.5R 6/11, and Moderate Red, 2.5R 4/10, with an area at the base between white and Brilliant Yellow Green, 2.5GY 9/8. The inner surface of the inside petal was from near Strong Reddish Orange, 7.5R 5/13, to near Dark Red, 2.5R 3/7, with an area at the base between white and near Brilliant Yellow Green, 2.5GY 9/8.

The general color effect of the newly opened flower which was grown in *warm, sunny weather* was near Strong Reddish Orange, 7.5R 5/13. The newly opened flower affected by *cool, overcast weather* was between Strong Reddish Orange, 7.5R 5/13, and Dark Red, 5R 3/7. After the bloom had been open for three days, the bloom grown in *warm, sunny weather* was near to but brighter than Strong Reddish Orange, 7.5R 5/13, while the flower affected by *cool, overcast weather* was still between Strong Reddish Orange, 7.5R 5/13, and Dark Red, 5R 3/7.

The petals drop off cleanly, after which the peduncle falls, from an abcission layer formed at its base.

In Southern California, the flower persists on the bush in the garden from three to five days in the month of October. Roses grown outdoors, but kept indoors at living-room temperatures, likewise persist from three to five days, in the month of October.

REPRODUCTIVE ORGANS

Stamens: There are an average number of stamens arranged irregularly about the pistils, a few being mixed with petaloids.

Filaments: The filaments are of medium length, from 5 to 10 mm. Their color is near Deep Purplish Pink, 7.5RP 6/12.

Anthers: The anthers are medium in size and open at various times. Their color on both upper and lower sides is near Brilliant Greenish Yellow, 7.5Y 9/8, sometimes lightly overlaid with near Strong Purplish Red, 10RP 4/12, with the margins near Moderate Orange Yellow, 10YR 8/10. This coloration of the anthers shows before the pollen is released.

Pollen: Pollen is somewhat sparse to moderate, and has a color which is near Moderate Orange Yellow, 10YR 8/10.

Pistils: The pistils are average to many, being approximately 100 in number.

Styles: The styles are moderately uneven, of average length, and are thin to average in caliper. They are somewhat loosely bunched.

Stigma: The stigma has a color near Brilliant Greenish Yellow, 10Y 9/9.

Ovaries: Most of the ovaries are enclosed in the calyx, although some protrude.

Hips: There are usually none.

Sepals: Drop off, with the receptacle and the peduncle, after the petals fall.

Seeds: This variety usually sets no seeds.

FOLIAGE

The compound leaves, which are normal to abundant, usually comprise from 3 to 7 leaflets. These are medium in size, moderately heavy and semi-glossy, and sometimes somewhat wrinkled. The leaflets are oval to ovate in shape, with apex acute, base obtuse, and margin simply serrate.

The color of the nature foliage is between Grayish Olive Green, 5GY 3/2, and Moderate Olive Green, 5GY 4/3, on its upper surface. The under surface is a grayish shade of a color lying between Moderate Yellow Green, 5GY 5/6, and Strong Yellow Green, 5GY 6/8.

The young growth, on its upper surface, is between Moderate Olive Green, 7.5GY 4/4, and Moderate Yellow Green, 5GY 5/6, heavily overlaid with near Dark Red, 2.5R 3/7. The color of the under surface is near Strong Yellow Green, 5GY 6/8, heavily overlaid with near Dark Red, 2.5R 3/7.

The rachis is average in size, the upper side being grooved, with some stipitate glands on the edges. The under side is sparsely prickly and with few stipitate glands.

The stipules are medium-length, moderately wide, and with medium-length points which turn out at an angle usually of more than 45°.

The plant has an average susceptibility to mildew.

GROWTH HABIT

The plant is bushy and much branched. Its growth is moderate, and the canes are medium in caliper.

The *main stems* are between Moderate Yellow Green, 5GY 5/6, and Moderate Olive Green, 5 GY 4/3. They bear several medium-length large prickles, which may be almost straight or hooked slightly downward, with medium-length narrow to broad base. The color of these large prickles is between Brownish Orange, 2.5YR 5/9, and Grayish Brown, 7.5YR 3/2. There are a few small prickles which have the same coloration as the large prickles. There are no hairs.

The *branches* are near Moderate Yellow Green, 5GY 5/6, in color. They bear several medium-length large prickles which are almost straight, but hooked slightly downward, and have medium-length moderately narrow bases. Their color is near Brownish Orange, 5YR 5/8. There are from few to many small prickles, whose color is the same as that of the large prickles. There are some stipitate glands, but no hairs.

*New shoots* are near Strong Yellow Green, 5GY 6/8, heavily overlaid where exposed to sunlight with near Dark Red, 2.5R 3/7. There are several large prickles, which are medium-length and hooked slightly downward, with medium-length, mode-rately narrow bases. Their color is between Dark Red, 5R 3/7, and Dark Red, 2.5R 3/7. There are a few small prickles, few to many stipitate glands, and no hairs.

I claim:

1. An asexually reproduced bush rose plant of the floribunda class, substantially as herein shown and described, being further characterized by combinations of a plurality of the following features, namely: the moderately low growing and moderately spreading habit of the plant and its tendency to bloom almost continuously throughout the growing season, although developing moderately massive display only at first Spring bloom; the relatively small size of the buds and the appearance that the bloom grows until it is fully open; the strong but sometimes bending peduncles, of average length and caliper, which drop off after the petals fall; the sepals which only occasionally extend beyond the tip of the bud; the flowers, which range from 2¾" to 3¾" in diameter with semi-double to double petalage and have from 19 to 25 petals and 2 to 8 petaloids; the absence of fragrance; and the color stability of the bright reddish orange petals, which last-named characteristic is an outstanding feature of the bloom.

No references cited.

ROBERT E. BAGWILL, Primary Examiner